United States Patent
Wolf et al.

(10) Patent No.: US 6,316,533 B1
(45) Date of Patent: Nov. 13, 2001

(54) COMPOSITION FOR TREATING TANNED LEATHER, AND ITS PREPARATION

(75) Inventors: Gerhard Wolf, Ketsch; Georg Igl, Weissach im Tal; Thomas Grösser, Ludwigshafen; Adolf Stübinger, Frankenthal; Jürgen Werner, Bad Dürkheim; Erhard Guenther, Hassloch, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/367,843

(22) PCT Filed: Feb. 23, 1998

(86) PCT No.: PCT/EP98/01025

§ 371 Date: Aug. 26, 1999

§ 102(e) Date: Aug. 26, 1999

(87) PCT Pub. No.: WO98/38341

PCT Pub. Date: Sep. 3, 1998

(30) Foreign Application Priority Data

Feb. 26, 1997 (DE) .............................................. 197 07 713

(51) Int. Cl.$^7$ ................. C08J 5/10; C08L 61/00
(52) U.S. Cl. .................... 524/158; 524/156; 524/284; 524/296
(58) Field of Search ..................................... 524/156, 158, 524/296, 284

(56) References Cited

U.S. PATENT DOCUMENTS

| 4,042,321 | * | 8/1977 | Backer et al. | 8/94.26 |
| 4,526,581 | * | 7/1985 | Prentiss et al. | 8/94.33 |
| 4,810,251 | * | 3/1989 | Traubel et al. | 8/94.23 |
| 4,822,372 | * | 4/1989 | Forster et al. | 8/94.24 |

FOREIGN PATENT DOCUMENTS

| 11 26 888 | 4/1962 | (DE) . |
| 15 45 192 | 3/1970 | (DE) . |
| 2 163 108 | 7/1973 | (FR) . |
| 2 270 327 | 12/1975 | (FR) . |

* cited by examiner

*Primary Examiner*—James J. Seidleck
*Assistant Examiner*—U. K. Rajguru
(74) *Attorney, Agent, or Firm*—Oblon, Spivak, McClelland, Maier & Neustadt, P.C.

(57) ABSTRACT

A composition containing (A) one or more aromatic sulfonates, (B) one or more aldehyde resins and (C) a buffer and is prepared and used for treating, in particular neutralizing, leather tanned with mineral compounds or mineral-free compounds.

25 Claims, No Drawings

COMPOSITION FOR TREATING TANNED LEATHER, AND ITS PREPARATION

The present invention relates to a composition containing (A) one or more aromatic sulfonates, (B) one or more aldehyde resins and (C) a buffer, the preparation of this composition and the use for treating, in particular for neutralizing, leather tanned with mineral or mineral-free compounds.

For the production of leather and pelts, animal skins are tanned with tanning agents, with the result that the skins are converted into resistant leathers of pelts. The tanning agents, which essentially result in crosslinking of the collagen fibers of the skin, can be divided into inorganic or mineral and organic tanning agents. The organic tanning agents may furthermore be of synthetic or vegetable origin.

Mineral tanning, in particular chrome tanning, is of considerable importance for the production of leathers and pelts. For example, 90% of all leathers are chrome tanned. In chrome tanning, the skin absorbs chrome(III) salts which cross link the collagen fibers owing to complex formation with the carboxyl groups of the collagen. The resulting intermediates of the chrome tanning are commercially available as semifinished products, i.e. wetblues, and are ideal for further processing to give a very wide range of leather articles. Retanning, in which the actual leather character is established, is generally necessary for this purpose.

The retanning is carried out as a rule with anionic substances which may originate from the class consisting of the synthetic or vegetable tanning agents, for example including resin tanning agents, lignin sulfonates, polymeric tanning agents, aldehydes, paraffin sulfonyl chlorides, polyphosphates or inert fillers. Furthermore, anionic fatliquoring agents are used in the retanning for the production of supple and water repellent leather, and anionic dyes are used for the production of dyed leather.

A fundamental problem in the retanning of, for example, chrome leather with anionic substances is, however, that the cationic character of the tanned leather may rapidly cause the anionic substances to react, with the result that the substances cannot penetrate into the leather or cannot penetrate deeply enough.

This generally leads to superficial and nonuniform deposition of the substances on the leather and overloading of the grain. The consequences may be an unattractive appearance of the grain, loose grain, poor leather properties and cracking of the grain. Even precipitation of the substances on the leather surface is possible.

As a rule, the retanning of tanned leather is therefore preceded by neutralization, which is intended to weaken or reduce the cationic character of the leather but may also intervene in the chemistry of the tanning. The neutralization should therefore be neither insufficient nor excessive in its intensity. Insufficient neutralization does not adequately solve the abovementioned problems and can, for example, also be a cause of a poor shelf-life of the leathers. Overneutralization on the other hand is often the cause of loose grain in the leather.

Oveneutralization is easily achieved with strong neutralizing agents, such as sodium carbonate, sodium bicarbonate or borax, which are therefore nowadays often used in combination with milder agents. With mild neutralizing agents, e.g. sodium formate, calcium format, sodium acetate, sodium sulfite, sodium thiosulfate or sodium polyphosphate, over neutralization is generally ruled out. However, the disadvantage of these agents is that the pH desired in the case of specific leather types cannot be achieved.

Also advantageous in the neutralizaton is the use of salts of organic and inorganic acids having a buffer effect, e.g. formates, acetates, oxalates, adipates, glutarates, citrates, lactates, carbonates, bicarbonates, polycarbonates, basic carbonates, silicates, borates or phosphates, so that the pH range desired for specific leather types can be more exactly controlled.

In addition to the salts having a buffer effect, tanning sulfonic acids, in particular based on naphthalene sulfonic acid/formaldehyde condensates, in combination with salts of acids having a buffer effect are also frequently used. Here, there is an interaction between the tanning sulfonic acids and, for example, the chromium complexes, with the displacement of sulfato groups and liberation of sulfuric acid. The liberated sulfuric acid is neutralized by the buffer. However, the disadvantage of such agents is that the leathers are strongly bleached and additional dye must therefore be used to obtain a desired dyeing of the leathers. In addition, the dyeings are less brilliant. Furthermore, the leathers are generally softer and less tight-grained, which is disadvantageous in particular for the upper leather sector.

It an object of the present invention to provide a composition and/or a process in which the disadvantages described above can be avoided or at least reduced. We have found that this object is achieved by a composition containing (A) one or more aromatic sulfonates, (B) one or more aldehyde resins and (C) one or more buffers.

It should be mentioned here that it is precisely the combination of the individual components (A), (B) and (C) and in particular the use of aldehyde resins as component (B), especially the use of aldehyde resins after their reaction with salts of sulfurous acid, which give rise to the surprising advantages of the novel composition. A further advantageous improvement in the novel composition can be achieved by a higher degree of sulfonation of the aromatic sulfonates as component (A).

The aromatic sulfonate according to (A) is generally selected from a sulfonated benzene and its derivatives, in particular toluene, phenol, cresol or resorcinol; sulfonated polycyclic aromatic compounds and their derivatives, in particular naphthalene, naphthol, (hydroxy)diaryl sulfones or (hydroxy)diaryl ethers, where aryl is preferably phenyl; sulfonated oligophenyls or their derivatives, preferably biphenyl or terphenyl; or mixtures thereof. In particular, naphthalene, toluene and xylene are suitable as starting materials.

In a further embodiment, the aromatic sulfonate according to (A) is a condensate of one or more aromatic sulfonates and an aliphatic aldehyde, preferably formaldehyde and/or acetaldehyde, in particular formaldehyde, or a condensate of one or more aromatic sulfonates and a condensate of one or more amides of carbonic acid and an aliphatic aldehyde, preferably formaldehyde and/or acetaldehyde, in particular formaldehyde. Suitable amides of carbonic acid are in particular urea and/or derivatives or urea, e.g. semicarbazide, guanidine, dicyandiamide and/or dicyandiamide derivatives, such as melamine. A urea/formaldehyde condensate, a melamine/formaldehyde condensate and/or melamine/urea/formaldehyde condensate are particularly preferred, especially a urea/formaldehyde condensate.

Advantageously, the sulfonated aromatic compound, which may be monosulfonated or polysulfonated, is prepared from a molar equivalent of an aromatic compound and 1–5, preferably 2–4, in particular about 3–4, molar equivalents of $SO_3$. Preferably, the aromatic sulfonate is a mixture of monosulfonated and polysulfonated compounds, in particular a mixture of compounds having different degrees of polysulfonation, especially disulfonated or trisulfonated compounds. Concentrated sulfuric acid, for example 95–98% strength sulfuric acid, or fuming sulfuric acid, for example 24% oleum (2 mol of $SO_3$), preferably serves as the $SO_3$ source. The reaction with concentrated or fuming sulfuric acid is preferably effected at about 100–160° C., in particular about 130–150° C., for about 1–4, preferably about 2, hours. The sulfonation products in this preferred process are in general polysulfonated, and, depending on the molecular ratio of aromatic compound to $SO_3$, Up to 50% by weight of free sulfate may additionally be present in the end product. The product is then generally brought to a pH of about 6–10, preferably with sodium hydroxide solution.

The preparation of condensates of sulfonated aromatic compound and formaldehyde or formaldehyde/urea condensates is generally known and is described in more detail, for example, in DE 28 43 233, for a β-naphthol sulfonic acid/formaldehyde or a naphthalene sulfonic acid/formaldehyde condensate as an example, or in DE 21 13 096, for a naphthalene sulfonic acid/formaldehyde/urea condensate as an example.

In another preferred embodiment, the aldehyde resin according to (B) is reacted by condensation of one or more aliphatic aldehydes, preferably formaldehyde and/or acetaldehyde, in particular formaldehyde, with one or more nitrogen-containing compounds; in particular, the aldehyde resin is reacted by simultaneous or subsequent condensation of one or more aliphatic aldehydes with one or more nitrogen-containing compounds and one or more salts of sulfurous acid, especially with sodium hydrogen sulfite. Advantageously, the nitrogen-containing compound is urea, melamine, dicyanamide and/or guanidine, preferably urea. For example, about one molar equivalent of a nitrogen-containing compound, preferably urea, is reacted with about 2–3 molar equivalents of an aliphatic aldehyde, preferably formaldehyde, at a pH of about 7 10 and at about 70–90° C. for about 1–3 hours and the condensate is preferably then reacted with about 1–3 molar equivalents of one or more salts of sulfurous acid, preferably sodium hydrogen sulfite, at a pH of about 7–10 and at about 90–105° C. for about 2–4 hours. The preparation of a condensate of melamine, urea, formaldehyde and hydrogen sulfite is described in more detail, for example, in EP 0 063 319.

In yet another preferred embodiment, the buffer or buffers according to (C) contains one or more salts of one or more acids having a buffer effect, preferably in a pH range of about 3–7, in particular of about 3–5. The choice of the suitable buffer for the corresponding leathers can be easily made, for example, on the basis of titration curves and is also described in more detail, for example, in Bibliothek des Leders, Volume 3, pages 211–233 (ed. H. Herfeld, Umschau-Verlag/Frankfurt, 1985). In particular, it is preferable if said acid is an organic acid, especially an organic mono- and/or dicarboxylic acid. For example, the salt of the organic acid is preferably a formate, acetate, carbonate, basic carbonate, bicarbonate, polycarbonate, citrate, glutamate, lactate, adipate, glutarate, succinate, oxalate, malonate, tartrate, phthalate, fumarate or maleate, the sodium salts being particularly preferred. In particular, a mixture of succinate, glutarate and adipate comprising preferably about 20–30% by weight of succinate, about 40–50% by weight of glutarate and about 20–30% by weight of adipate and, if required, additionally about 10–80% by weight of formate is preferred. It is also preferred if said acid is an inorganic acid, in particular sulfurous acid, phosphoric acid, silicic acid, boric acid and/or nitrous acid.

The amounts of the individual components (A), (B) and (C) in the novel composition are in particular as follows: component (A): about 5–80, preferably about 20–60, especially about 30–50, % by weight; component (B): about 5–80, preferably about 10–40, especially about 15–25, % by weight; component (C): about 10–80, preferably about 20–60, especially about 30–40, % by weight.

In general, the novel composition is prepared by simply mixing the components (A), (B) and (C) and/or by preparing the individual components in a one-pot reaction.

The present invention therefore furthermore relates to a process for the preparation of the novel composition by mixing the components (A), (B) and (C) and/or preparing the components (A), (B) and/or(C) in a one-pot reaction, preferably with the amounts described above and by the methods described above.

The novel composition is advantageous for the treatment of tanned leather.

The present invention also therefore relates to a process and the use of the novel composition for treating tanned leather, in particular for neutralizing tanned leather, especially for treating or neutralizing leather tanned with mineral compounds. The novel composition is preferably suitable for treating leather tanned with chromium, aluminum, zirconium, titanium and/or iron salts, in particular with chromium(III) salts, especially with chromium(III) sulfate (wetblue). Use for wetwhite leathers, i.e. leathers pretanned with organic tanning agents, is also possible. In particular, leathers tanned with aldehyde, e.g. glutaraldehyde or formaldehyde, are to be understood here. These also include leathers tanned with synthetic tanning agents or tanned with combinations of synthetic tanning agents and tanning agents of vegetable origin (Döppert S. et al. (1994), Das Leder, 12, 272).

The present invention surprisingly makes it possible to improve the brilliance and depth of color of the leathers, the bleaching effect, described above, of known neutralizing tanning agents not being observed or essentially not being observed. The leathers generally have a very round, pleasant handle and are outstandingly tight-grained. Moreover, improved grain fineness of the leather surface is achieved.

The examples which follow illustrate the invention without restricting it.

EXAMPLES

Example 1

187.2 g of 24% oleum (2 mol of $SO_3$) are added to 64.8 g of naphthalene (0.5 mol) at 100–110° C. in the course of 1 hour and the mixture is heated to 150° C. and kept at this temperature for 1 hour. After cooling to 120° C., 180 g of water are added and the pH is brought to 9 with about 265 g of 50% NaOH.

190 g of 30% formaldehyde (1.9 mol) and 69.8 g of 65.5% urea solution (0.75 mol) are added and condensation is carried out for 2 hours at 80° C. Thereafter, 325 g of 40% $NaHSO_3$ (1.25 mol) are added and the pH is brought 9 with 50% NaOH. Stirring is carried out for 3 hours at 100–103° C.

Thereafter, 285 g of 50% NaOH are added dropwise and at the same time 265 g of an industrial mixture of succinic acid (20–30%), glutaric acid (40–50%) and adipic acid (20–30%) are added.

Solids content: 46%.

Example 2

360 g of 95% $H_2SO_4$ (3.5 mol) are added to 184 g of toluene (2 mol) at 90° C. in the course of 45 minutes and the mixture is then heated to 140–145° C. in the course of 1 hour. This temperature is maintained for 3 hours. Thereafter, the mixture is cooled to 100° C., 250 g of water are added and the pH is brought to 9 with 50% NaOH.

198 g of 40% $NaHSO_3$ (0.75 mol), 150 g of 30% formaldehyde (1.5 mol) and 45 g of urea (0.75 mol) are then added. The reaction mixture is heated to 90° C., kept at this temperature for 4 hours and cooled to 80° C., and 240 g of the dicarboxylic acid mixture stated in Example 1 and simultaneously 250 g of 50% NaOH are added. 150 g of water and 25.5 g of sodium formate are then added.

Solids content: 48%.

Example 3

490 g of 95% $H_2SO_4$ (4.75 mol) are added to 212 g of xylene (isomer mixture, 2 mol) at 90° C. in the course of 30 minutes and the mixture is then heated to 140° C. in the course of 20 minutes. This temperature is maintained for 3 hours. Thereafter, the mixture is cooled to 100° C. and 250 g of water are added. The pH is brought to 9 with 50% NaOH, after which 45 g of urea (0.75 mol) and 175 g of 30% formaldehyde (1.75 mol) are added and the mixture is heated to 80° C. and is stirred at this temperature for 2 hours. Thereafter 264 g of 40% $NaHSO_3$ (1 mol) are added and stirring is continued for a further 4 hours at 90° C. 200 g of water, 294 g of dicarboxylic acid mixture is stated in Example 1 and 50 g of formic acid are then added and the pH is brought to 7 with about 500 g of 50% NaOH.

Solids content: 47%.

Comparative Example A 331 g of concentrated $H_2SO_4$ (3.24 mol) are added to 142.5 g of naphthalene (1.11 mol) at 100–110° C. for 30 minutes and the mixture is heated to 140° C. and kept at this temperature for 5 hours. Thereafter, it is cooled to 80° C. and 400 g of water, 117 g of dicarboxylic acid mixture stated in Example 1 and 180 g of sodium formate are added. The pH is then brought to 7 with about 500 g of 50% NaOH. Solids content: 48%.

Comparative Example B 850 g of a 30% strength aqueous solution of a commercial naphthalene sulfonic acid/formaldehyde condensate are heated to 50° C. and 265 g of dicarboxylic acid mixture stated in Example 1 are added. The mixture is brought to pH 7 with about 280 g of 50% NaOH.

Solids content: 47%.

Embodiments: Production of Upper Leather

Wetblue usually produced from cattle hides is shaved to 1.8 mm and washed with 200% (based in each case on shaved weight) of water. Drumming is then carried out in 100% aqueous liquor with 3% of a tanning agent mixture analogous to Example 1 (calculated relative to solids content) for 90 minutes at 30° C. The pH of the liquor is then about 4.5. The liquor is drained off and washing is effected with 200% of water. Drumming is carried out for 20 minutes in 100% liquor with 2% of a commercial polymer tanning agent based on acrylic acid and then 6% of vegetable tanning agent are added. After 40 minutes, the liquor is drained off, washing is effected and dyeing and fatliquoring are carried out using commercial dyes and fatliquoring agents.

A leather having excellent fine-grained and tight-grained characteristics and a very dark, brilliant and uniform dyeing in which the dullness caused in the dyeing by the vegetable tanning agent no longer occurs. The leather is very full and has a round handle. Similar results are obtained if the products from Examples 2 and 3 are used as the neutralizing component. Comparative Example A gives very nonuniform, dull dyeings and very hard, frail leathers.

Comparative Example B gives very light leathers which are substantially more loose-grained than the leathers which are treated with the products according to Examples 1–3.

We claim:
1. A composition, comprising:
   (A) from 5 to 80% by weight of one or more aromatic sulfonates selected from the group consisting of sulfonated benzene and derivatives thereof, sulfonated polycyclic aromatic compounds and derivatives thereof, sulfonated oligophenyls and derivatives thereof, and mixtures thereof, prepared from one molar equivalent of the aromatic compound and
   (B) from 5 to 80% by weight of one or more aldehyde resins prepared from one molar equivalent of a nitrogen-containing compound, 2–3 molar equivalents of an aliphatic aldehyde and, optionally, 1–3 molar equivalents of one or more salts of sulfurous acid at a pH of from about 7 to 10; and
   (C) from 10 to 80% by weight of one or more buffers, prepared by mixing (A), (B) and (C) and/or preparing the (A), (B) and/or (C) in a one-pot reaction.
2. The composition of claim 1, wherein the aromatic sulfonate is selected from the group consisting of sulfonated benzene and derivatives thereof, sulfonated polycyclic aromatic compounds and derivatives thereof, and mixtures thereof.
3. The composition of claim 2, wherein the aromatic sulfonate is a condensate of one or more aromatic sulfonates as claimed in claim 2 and an aliphatic aldehyde, or a condensate of one or more aromatic sulfonates as claimed in claim 2 and a condensate of one or more amides of carbonic acid and an aliphatic aldehyde.
4. The composition of claim 3, wherein the aliphatic aldehyde is formaldehyde and/or acetaldehyde.
5. The composition of claim 3, wherein the amide of carbonic acid is urea and/or a derivative of urea.
6. The composition of claim 1, wherein the aromatic sulfonate is a monosulfonated and/or a polysulfonated aromatic compound and/or a mixture of aromatic compounds having different degrees of polysulfonation.
7. The composition of claim 6, wherein the aromatic sulfonate is a disulfonated or trisulfonated aromatic compound.
8. The composition of claim 1, wherein the sulfonated aromatic compound is prepared from one molar equivalent of an aromatic compound and 1–5, molar equivalents of $SO_3$.
9. The composition of claim 1, wherein (B) is prepared by condensation of one or more aliphatic aldehydes with one or more nitrogen-containing compounds.
10. The composition of claim 9, wherein the aldehyde resin is prepared by simultaneous or subsequent condensation of one or more aliphatic aldehydes with one or more nitrogen-containing compounds and one or more salts of sulfurous acid.
11. The composition of claim 9, wherein the aliphatic aldehyde is formaldehyde and/or acetaldehyde.
12. The composition of claim 9, wherein the nitrogen-containing compound is selected from the group consisting of urea, melamine, dicyanamide and guanidine.
13. The composition of claim 9, wherein the aldehyde resin is prepared from one molar equivalent of a nitrogen- containing compound, 2–3 molar equivalents of an aliphatic aldehyde and, optionally 1–3 molar equivalents of one or more salts of sulfurous acid.

14. The composition of claim 1, wherein (C) contains one or more salts of one or more acids having a buffer effect.

15. The composition of claim 14, wherein said acid is an organic acid.

16. The composition of claim 14 wherein said acid is an organic mono- and/or dicarboxylic acid.

17. The composition of claim 14, wherein said acid is selected from the group consisting of a formate, acetate, carbonate, basic carbonate, bicarbonate, citrate, glutamate, lactate, adipate, glutarate, succinate, oxalate, malonate, tartrate, phthalate, fumarate and maleate.

18. The composition of claim 14, wherein said acid is an inorganic acid.

19. The composition of claim 14, wherein said acid is sulfurous acid, phosphoric acid, silicic acid, boric acid and/or nitrous acid.

20. The composition of claim 1, comprising about 20–60% by weight of (A), about 10–40% by weight of (B), and about 20–60% by weight of (C).

21. A process for preparing a composition as claimed in claim 1, wherein components (A), (B) and (C) are mixed and/or the components (A), (B) and/or (C) are prepared in a one-pot reaction.

22. A process for treating tanned leather, wherein the tanned leather is treated with a composition as claimed in claim 1.

23. A process as claimed in claim 22, wherein the leather is leather tanned with mineral compounds.

24. A process as claimed in claim 23, wherein the mineral compounds are selected from the group consisting of chromium, aluminum, zirconium, titanium and iron salts.

25. A process as claimed in claim 22 wherein said tanned leather is neutralized.

* * * * *